United States Patent [19]

Klein et al.

[11] Patent Number: 5,053,392

[45] Date of Patent: Oct. 1, 1991

[54] NOVEL ARGININE, GLYCINE, ASPARTIC ACID DERIVATIVES AS PLATELET-AGGREGATION INHIBITORS

[75] Inventors: Scott I. Klein, Audubon; Bruce F. Molino, Hatfield, both of Pa.

[73] Assignee: Rhone-Poulenc Rorer Pharmaceuticals Inc., Fort Washington, Pa.

[21] Appl. No.: 444,484

[22] Filed: Dec. 1, 1989

[51] Int. Cl.$^5$ .............................................. A61K 37/00
[52] U.S. Cl. ........................................ 514/18; 514/19; 530/330; 530/331; 548/953
[58] Field of Search ................... 514/18, 19; 530/330, 530/331; 548/953

[56] References Cited

U.S. PATENT DOCUMENTS 4,683,291 7/1987 Zimmerman et al. .

FOREIGN PATENT DOCUMENTS 0319506 12/1988 European Pat. Off. .
2608160 12/1986 France .

OTHER PUBLICATIONS

Chou et al., "Prediction of Protein Conformation", Biochemistry, vol. 13, No. 2 (1974), pp. 222-224.
Pierschbacher et al., "Influence of Sterochemistry of the Sequence", J. Biol. Chem., vol. 262, No. 86, pp. 17294-17298 (1987).
Ginsberg et al.; "Inhibition of Fibronectin Binding to Platelets by Proteolytic Fragments and Synthetic Peptides Which Support Fibroblast Adhesion"; The Journal of Biological Chemistry, vol. 260, No. 7, Apr. 10, 1985; pp. 3931-3936.
Gartner et al.; "The Tetrapeptide Analogue of the Cell Attachment Site of Fibronectin Inhibits Platelet Aggregation and Fibrinogen Binding to Activated Platelets", The Journal of Biological Chemistry; vol. 260, No. 22, Oct. 5, 1985; pp. 11891-11894.
Haverstick et al., "Inhibition of Platelet Adhesion to Fibronectin, Fibrinogen, and vWF Substrates by a Synthetic Tetrapeptide Derived From the Cell-Binding Domain of Fibronectin"; Blood, vol. 66, No. 4 (Oct.), 1985: pp. 946-952.
Plow et al., "Inhibition of Fibrinogen Binding to Human Platelets by the Tetrapeptide glycyl-L--prolyl-L-arginyl-L-proline"; Proc. Natl. Acad. Sci. U.S.A., vol. 79, pp. 3711-3715, Jun. 1982.
Plow et al., "The Effect of Arg-Gly-Asp-Containing Peptides on Fibrinogen and von Willebrand Factor Binding to Platelets"; Proc. Natl. Acad. Sci. U.S.A., vol. 82, pp. 8057-8061, Dec. 1985.
Santoro et al. ; "Competition for Related but Nonidentical Binding Sites on the Glycoprotein IIb-IIIa Complex by Peptides Derived from Platelet Adhesive Proteins"; Cell, vol. 48, 867-873, Mar. 13, 1987.
Ruggeri et al.; "Inhibition of Platelet Function with Synthetic Peptides Designed to be High-Affinity Antagonists of Fibrinogen Binding to Platelets"; Proc. Natl. Acad. Sci. U.S.A.; vol. 83, pp. 5708-5712, Aug. 1986.
Ruoslahti et al. ; "Arg-Gly-Asp: A Versatile Cell Recognition Signal", Cell, vol. 44, 517-518, Feb. 28, 1986.

*Primary Examiner*—Lester L. Lee
*Assistant Examiner*—E. J. Kraus
*Attorney, Agent, or Firm*—Imre (Jim) Balogh; James A. Nicholson

[57] ABSTRACT

Disclosed are novel amino acid derivatives of the formula:

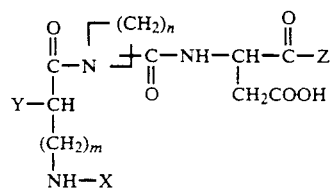

wherein
X is H, amidino or

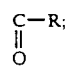

Y is H, amino or

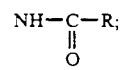

Z is

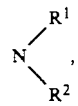

OR$_1$ or a naturally occurring L-amino acid, bounded to the carbon atom at the α-amino position;
R is alkyl, aryl or aralkyl;
R$_1$ and R$_2$ are independently H, alkyl, aryl, aralkyl or allyl;
m is 1 through 5;
n is 0 through 4; and
pharmaceutically acceptable salts thereof, that inhibit platelet aggregation and thrombus formation in mammalian blood.

8 Claims, No Drawings

NOVEL ARGININE, GLYCINE, ASPARTIC ACID DERIVATIVES AS PLATELET-AGGREGATION INHIBITORS

BACKGROUND OF THE INVENTION

1. Field of the Invention

This invention relates to novel compounds having anti-thrombotic activity. More particularly, the invention relates to novel peptides and pseudopeptides that inhibit platelet aggregation and thrombus formation in mammalian blood and thereby are useful in the prevention and treatment of thrombosis associated with certain disease states, such as, myocardial infarction, stroke, peripheral arterial disease and disseminated intravascular coagulation.

Haemostasis, the biochemistry of blood coagulation, is an extremely complex and as yet not completely understood phenomena whereby normal whole blood and body tissue spontaneously arrest bleeding from injured blood vessels. Effective haemostasis requires the combined activity of vascular, platelet and plasma factors as well as a controlling mechanism to prevent excessive clotting. Defects, deficiencies, or excesses of any of these components can lead to hemorrhagic or thrombotic consequences.

Platelet adhesion, spreading and aggregation on extracellular matrices are central events in thrombus formation. These events are mediated by a family of platelet adhesive glycoproteins, i.e., fibrinogen, fibronectin, and von Willebrand factor. Fibrinogen is a co-factor for platelet aggregation, fibronectin supports platelet attachments and spreading reactions, and von Willebrand factor is important in platelet attachment to and spreading on subendothelial matrices. The binding sites for fibrinogen, fibronectin and von Willebrand factor have been located on the platelet membrane glycoprotein complex IIb/IIIa.

Adhesive glycoprotein, like fibrinogen, do not bind with normal resting platelets. However, when a platelet is activated with an agonist such as thrombin or adenosine diphosphate, the platelet changes its shape, perhaps making the GPIIb/IIIa binding site accessible to fibrinogen. The novel molecules described in this invention may block the fibrinogen receptor, thus inhibiting platelet aggregation and subsequent thrombus formation. Pharmaceutical agents and/or compositions possessing such an inhibiting effect may be provided for the prophylaxis and treatment of thrombogenic diseases, such as myocardial infarction, stroke, peripheral arterial disease and disseminated intravascular coagulation.

2. Reported Developments

It has been observed that the presence of Arg-Gly-Asp (RGD) is necessary in fibrinogen, fibronectin and von Willebrand factor for their interaction with the cell surface receptor (Ruoslahti E., Pierschbacher, Cell 1986, 44, 517-18). Two other amino acid sequences also seem to take part in the platelet attachment function of fibrinogen, namely, the Gly-Pro-Arg sequence, and dodecapeptide, His-His-Leu-Gly-Gly-Ala-Lys-Gln-Ala-Gly-Asp-Val, sequence. Synthetic small peptides containing the RGD or dodecapeptide units show activity: they bind to the platelet receptor and competitively inhibit binding of fibrinogen, fibronection and von Willebrand factor as well as inhibiting aggregation of activated platelets (Plow et al. Proc. Natl. Acad. Sci. U.S.A. 1985, 82, 8057-61; Ruggeri et al. Proc. Natl. Acad. Sci. U.S.A. 1986, 5708-12; Ginsberg, et al. J. Biol. Chem. 1985, 260, 3931-36; and Gartner et al. J. Biol. Chem. 1987, 260, 11,891-94).

The present invention is directed to novel peptides and pseudopeptides which inhibit platelet aggregation and subsequent thrombus formation.

SUMMARY OF THE INVENTION

The present invention comprises peptides and pseudopeptides of the general formula:

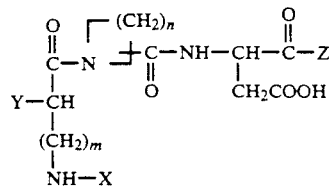

wherein:
X is H, amidino or

Y is H, amino or

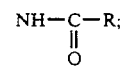

Z is

$OR_1$ or a naturally occurring L-amino acid, bounded to the carbon atom at the α-amino position;
R is alkyl, aryl or aralkyl;
$R_1$ and $R_2$ are independently
H,
alkyl,
aryl,
aralkyl or
allyl;
m is 1 through 5;
n is 0 through 4; and
pharmaceutically acceptable salts thereof.

In accordance with the present invention, novel compounds are provided which inhibit platelet aggregation by inhibiting fibrinogen binding to activated platelets and other adhesive glycoproteins involved in platelet aggregation and blood clotting. Compounds of the present invention, as tested by methods predictive of anti-thrombotic activity, are believed to be useful in the prevention and treatment of thrombosis associated with certain diseased states, such as myocardial infarction, stroke, peripheral arterial disease and disseminated intravascular coagulation.

The present compounds may also be useful for the treatment of certain cancerous diseases since they may interfere with adhesive interactions between cancer cells and the extracellular matrix (Journ. of Biol. Chem., Vol. 262, No. 36 1987, pp. 17703-17711; Science, Vol.

233, 1986, pp. 467–470; and Cell, Vol. 57, 59–69, April 1989).

The invention also comprises pharmaceutical compositions useful for the prevention and treatment of thrombosis comprising an aforsaid compound in a pharmaceutically acceptable carrier.

Another aspect of this invention comprises a method for the prevention and treatment of thrombosis associated with the aforsaid diseases.

DETAILED DESCRIPTION OF THE INVENTION

As used herein: alkyl represents a saturated aliphatic hydrocarbon, either branched or straight-chained, with up to about 10 carbon atoms. Preferred alkyl includes methyl, ethyl, n-propyl, isopropyl, butyl, sec-butyl, t-butyl, amyl and hexyl; aryl preferably denotes phenyl and naphthyl; and aralkyl means an alkyl group substituted by an aryl radical, the preferred aralkyl groups being benzyl and phenethyl. The naturally occurring L-amino acids include:

Val
Ser
Phe
Gly
Leu
Ile
Ala
Tyr
Trp
Thr
Pro
Arg
Asn
Asp
Cys
Glu
His
Lys and
Met.

The compounds of the present invention may be readily prepared by standard solid phase or solution phase peptide synthesis techniques using starting materials and/or intermediates available from chemical supply companies such as Aldrich and Sigma or may be synthesized by standard organic chemical techniques. (H. Paulsen, G. Merz, V. Weichart, "Solid-Phase Synthesis of O-Glycopeptide Sequences", Angew. Chem. Int. Ed. Engl. 27 (1988); H. Mergler, R. Tanner, J. Gosteli, and P. Grogg, "Peptide Synthesis by a Combination of Solid-Phase and Solution Methods I: A New Very Acid-Labile Anchor Group for the Solid-Phase Synthesis of Fully Protected Fragments. Tetrahedron letters 29, 4005 (1989); Merrifield, R. B., "Solid Phase Synthesis after 25 years: The Design and Synthesis of Antagonists of Glucagon", Makromol. Chem. Macromol. Symp. 19, 31 (1989)).

The solid phase method is represented schematically as follows:

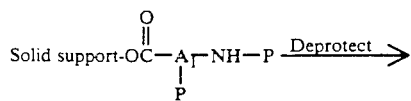

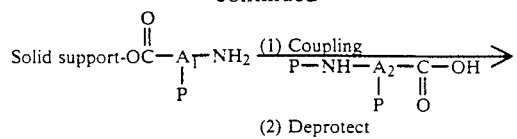

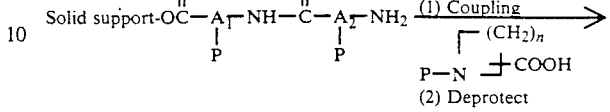

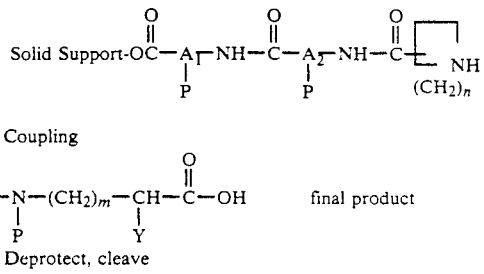

wherein: the solid support may be, but is not limited to, p-alkoxybenzylalcoholresin;

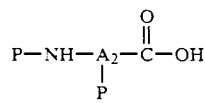

is a protected amino acid derivative;

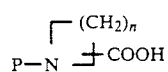

is a protected derivative of a nitrogen heterocycle carboxylic acid where n is 0, 1, 2, 3, or 4;

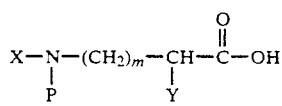

is an amino carboxylic acid derivative where X is H, amidino or

Y is H, amino or

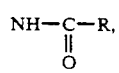

where R is alkyl, aryl or aralkyl.

In the process of making the desired compound, the amino acid derivatives are added one at a time to the insoluble resin to give the desired dipeptide resin derivative, then the nitrogen heterocycle carboxylic acid derivative is coupled to the N-terminal of the chain, followed by coupling of the amino carboxylic acid derivative. Any reactive functional groups of these derivatives are blocked by protecting groups to prevent cross reactions during the coupling procedures. These protecting groups include, but are not limited to, tertiary butoxycarbonyl (BOC), carbobenzoxy (CBZ), benzyl, t-butyl, 9-fluorenylimethoxycarbonyl (FMOC) and methoxy-2,3,6-trimethylbenzenesulfonyl (MTR). Upon completion of each coupling reaction, the α-amino protecting group is removed by standard procedures and the α-amino group is, in turn, coupled to a derivative having a free carboxylic acid function. The procedure is repeated until the desired product derivative is formed. The final product is obtained by deprotection and cleavage of the product from the resin by standard techniques.

Alternatively, the compounds of the present invention may be prepared in solution, i.e., without using a solid support. In a manner that is similar to the solid phase synthesis, the protected derivatives are coupled, then deprotected using standard procedures.

The invention will now be explained further by the following illustrative examples:

EXAMPLE 1

N-(5-guanidino pentanoyl)azetidine(2S)-carboxyl-Asp-Val

A. 0.5 g of N-(9-fluororenylmethoxycarbonyl)-L-valine-p-alkoxybenzyl alcohol resin ester (containing approximately 0.28 mmol of amino acid) was deprotected by shaking with 10 ml of 20% piperidine in dimethylformamide at room temperature for 1 hour. The mixture was filtered and the resin washed with methylene chloride to give L-valine p-alkoxybenzyl alcohol resin ester.

B. The product from Example 1A was shaken with 0.460 g N-FMOC L-aspartic acid β-t-butyl ester, 0.214 g 1-(3-dimethylaminopropyl)-3-ethylcarbodiimide hydrochloride (EDC), 0.151 g 1-hydroxybenzotriozole (HOBT) and 0.16 ml triethylamine in 10 ml of dimethylformamide for 1 hour at room temperature. The mixture was filtered, the resin derivative washed with methylene chloride, then deprotected as in Example 1A to give L-aspartyl-β-t-butyl ester-L-valine p-alkoxy-benzyl alcohol resin ester.

C. To a solution of 0.50 g of (S)-(−)-2-azetidine carboxylic acid in 15 ml of 10 aqueous sodium carbonate solution was added 1.3 g of 9-fluorenylmethyl chloroformate in 10 ml of dioxane, dropwise, while maintaining the temperature of the reaction mixture at 0° C. The reaction mixture was allowed to warm to room temperature and stirred for 3 hours, then poured into water and the aqueous solution was washed with ether. The aqueous layer was cooled to 0° C. and adjusted to a pH of 2 with 3N hydrochloric acid and extracted with ethyl acetate. The ethyl acetate solution was dried over magnesium sulfate, filtered, and evaporated in vacuo to give (S)-N-(9-fluorenylmethoxycarbonyl) azetidine-2-carboxylic acid.

D. The product from Example 1C was shaken with 0.271 g of N-FMOC azetidine-2-carboxylic acid, 0.160 g EDC, 0.113 g HOBT and 0.12 ml of triethylamine in 10 ml dimethylformamide for 3 hours at room temperature, then filtered, washed and deprotected as in Example 1A to give N-[(S)-azetidin-2-yl-carboxyl]-L-aspartyl-β-t-butyl ester-L-valine-p-alkoxybenzyl alcohol ester resin.

E. 5-guanidinopentanoic acid was prepared by the method of Miller, et al., Synthesis, 777 (1986), which is incorporated herein by reference. 2.00 g of 5-aminovaleric acid was dissolved in a solution of 2.35 g of potassium carbonate in 20 ml of water followed by the portionwise addition of 2.13 g aminoiminomethanesulfonic acid over 10 minutes. The solid which formed after stirring at room temperature overnight was collected and recrystallized from water. The guanidine was dissolved in dilute hydrochloric acid solution and the solution evaporated in vacuo. The residue was washed with 2-propanol which was then evaporated to give 5-guanidinopentanoic acid hydrochloride.

F. 0.218 g 5-guanidinopentanoic acid hydrochloride, 0.214 g EDC, 0.151 g HOBT, 0.16 ml triethylamine and the product from Example 1D were shaken together in 10 ml dimethylformamide for 3 hours. The mixture was filtered and the resin washed with methylene chloride. The product was deprotected and removed from the resin by treatment with 95% trifluoroacetic acid for 2 hours. The resin was filtered off and the filtrate diluted with 0.5N acetic acid. The solution was washed with ethyl acetate and the aqueous layer lyophilized to give N-(5-guanidinopentanoyl)-azetidine(2S)-carboxyl-Asp-Val as the trifluoroacetate salt.

EXAMPLE 2

N-(5-aminopentanoyl)-azetidin-(2S)-carboxyl-Asp-Val

A. A solution of 2.00 g 5-aminopentanoic acid and 3.62 g of sodium carbonate in 30 ml of water was cooled to 0° C. and 4.41 g of 9-fluorenylmethyl chloroformate in 10 ml of tetrahydrofuran was added dropwise. The mixture was allowed to warm to room temperature and stirred for 2 hours. The mixture was then diluted with water and washed with ether. The aqueous solution was cooled to 0° C. and adjusted to pH 2 with 3N hydrochloric acid. The resulting white solid was collected by filtration and dried to give N-(9-fluorenylmethoxycarbonyl)-5-amino-pentanoic acid.

B. 0.379 g N-FMOC-5-aminopentanoic acid, N-[azetidin-(2S)-carboxyl]-L-aspartyl-β-t-butyl ester-L-valine-p-alkoxybenzyl alcohol ester resin (prepared from 0.50 g N-FMOC-L-valine-p-alkoxybenzyl alcohol resin ester as in Examples 1A–D), 0.214 g EDC, 0.151 g HOBT and 0.16 ml triethylamine were shaken in 10 ml dimethylformamide for 2 hours at room temperature. The mixture was filtered and the resin derivative washed with methylene chloride. The FMOC protecting group was removed by treatment with 20% peperidine in DMF as in Example 1A. The t-butyl ester protecting group was removed, and the product cleaved from the resin by treatment with 95% trifluoracetic acid as in Example 1F, N-(5-aminopentanoyl)-azetidin-(2S)-carboxyl-Asp-Val as the trifluoroacetate salt, m.p. 64°–66° C.

EXAMPLE 3

N-(L-arqinyl)-azetidine-(2S)-carboxyl-Asp-Val 1.36 g Nα-FMOC-Nω-(4-methoxy-2,3,6-trimethylbenzenesulfonyl)-L-arginine, N-[azetidin-2S-carboxyl]-L-aspartyl-β-t-butyl ester-L-valine-p-alkoxybenzyl ester resin (prepared from 1.0 g N-FMOC-L-valine-p-alkoxybenzyl ester resin as in Example 1A–D), 0.428 g EDC, 0.302 g HOBT and 0.31 ml triethylamine were shaken together in 10 ml dimethylformamide for 2.5 hours at room temperature. The FMOC protecting group was removed by treatment with 10 ml 20% piperidine in DMF as in Example 1A. The t-butyl ester protecting group was removed, and the product cleaved from the resin, by treatment with 10 ml 95% trifluoroacetic acid for 2 hours at room temperature in the presence of 0.2 ml 1,2-ethanedithiol. The resin was filtered off and washed with trifluoroacetic acid. The solution was evaporated in vacuo at room temperature. The residue was treated with 100% trifluoracetic acid for 24 hours to remove the MTR protecting group. The solution was diluted with 0.5N aqueous acetic acid and this solution was washed with ethyl acetate. The aqueous layer was lyophilized to give N-[L-arginyl)-azetidine-(2S)-carboxyl-Asp-Val as the trifluoroacetate salt, m.p. 110°–112° C.

EXAMPLE 4

N-[1-(L-arginyl)piperidin-2-yl-carbonyl]-L-aspartyl-L-valine

A. Piperidine-2-carboxylic acid was treated as in Example 1C to give N-(9-fluorenylmethoxycarbonyl)-piperidine-2-carboxylic acid.

B. N-FMOC-piperidine-2-carboxylic acid was substituted for the azetidine carboxylic acid in Example 1D and treated as in Example 1D to give N-[piperidin-2-yl-carboxyl]-L-aspartyl-$\beta$-t-butyl ester-L-valine-p-alkoxybenzyl alcohol ester resin.

C. The product from Example 4B was substituted for azetidin-(2S)-carboxyl]-L-aspartyl-$\beta$-t-butyl ester-L-valine-p-alkoxybenzyl ester resin in Example 3 and treated as in Example 3 to give N-[1-(L-arginyl)piperidin-2-carboxyl]-L-aspartyl-L-valine as the ditrifluoroacetate salt, m.p. 109°–112° C.

EXAMPLE 5

L-Arginyl-L-prolyl-L-aspartyl-L-valine

A. 2.04 ml triethylamine was added to a solution of 1.4 g EDC in 50 ml of methylene chloride, followed by 3.0 g N-FMOC-L-aspartic acid $\beta$-t-butyl ester and 1.32 g L-valine-t-butyl ester and 0.985 g HOBT. The mixture was stirred at room temperature for 4 hours, diluted with ethyl acetate, washed with water and the organic layer dried over magnesium sulfate. This was filtered and the filtrate evaporated in vacuo to give N-(9-fluorenyl-methoxycarbonyl)-L-aspartyl-$\beta$-t-butyl ester-L-valine-t-butyl ester.

B. To 2.0 g of the product from Example 5A in 16 ml of methylene chloride was added 4 ml of piperidine. After stirring at room temperature for 1 hour the solvents were removed in vacuo to give L-aspartyl-$\beta$-t-butyl ester-L-valine-t-butyl ester.

C. The product from Example 5B was treated with 1.18 g N-FMOC-L-proline in the presence of 0.669 g EDC, 0.472 g HOBT and 0.5 ml triethylamine in methylene chloride as in Example 5A to give N-(9-fluorenylmethoxycarbonyl)-L-proyl-L-aspartyl-$\beta$-t-butyl ester-L-valine-t-butyl ester.

D The product from Example 5C was deprotected in a manner similar to that in Example 5B to give L-prolyl-L-aspartyl-$\beta$-t-butyl ester-L-valine-t-butyl ester.

E. 0.24 g of the product from Example 5D was coupled with 0.328 g N$\alpha$-FMOC-N$\omega$-MTR-L-arginine in the presence of 0.103 g EDC, 0.08 ml triethylamine and 73 mg HOBT in methylene chloride in a manner similar to that of Example 5A to give N$\alpha$-(9-fluorenylmethoxycarbonyl)-N$\omega$-(4-methoxy-2,3,6-trimethylbenzenesulfonyl)-L-arginyl-L-prolyl-L-aspartyl-$\beta$-butyl-t-ester-L-valine-t-butyl ester.

F. 0.36 g of the product from Example 5E was dissolved in 16 ml methylene chloride and 4 ml of piperidine was added, stirred for 45 minutes at room temperature and the solvent removed in vacuo. The residue was partitioned between methanol and hexane. The methanol layer was evaporated in vacuo and the residue subjected to flash chromatography in methanol/chloroform (1:1) to give N$\omega$-(4-methoxy-2,3,6-trimethylbenzenesulfonyl)-L-arginyl-L-prolyl-L-aspartyl-$\beta$-t-butyl ester-L-valine-t-butyl ester.

G. 0.26 g of the product from Example 5F was dissolved in 5 ml trifluoroacetic acid and 0.2 ml 1,2-ethanedithiol was added. This solution was stirred at room temperature for 24 hours. The solution then was evaporated in vacuo and the residue taken up in 0.5N acetic acid and this solution washed several times with ethyl acetate. The aqueous layer was lyophilized and the residue taken up in dioxane. Hydrogen chloride gas was then bubbled into the solution. The dioxane was removed in vacuo and the residue was crystallized from methanol/ether to give L-arginyl-L-prolyl-L-aspartyl-L-valine as the hydrochloride salt, m.p. 150° C. (dec.).

Compounds of the present invention were tested for inhibition of platelet aggregation using the following procedures:

I. Inhibition of Radiolabeled (125I) Fibrinogen Binding Assay, which is essentially based on the method described in Proc Natl. Acad. Sci. U.S.A. Vol. 83, pp. 5708–5712, August 1986, and is as follows.

Platelets are washed free of plasma constitutes by the albumin density-gradient technique. In each experimental mixture platelets in modified Tyrode's buffer are stimulated with human $\alpha$-thrombin at 22°–25° C. for 10 minutes ($3.125 \times 10''$ platelets per liter and thrombin at 01 N1H units/ml). Hirudin is then added at a 25-fold excess for 5 minutes before addition of the radiolabeled ligand and any competing ligand. After these additions, the final platelet count in the mixture is 22°–25° C., bound and free ligand are separated by centrifuging 50 $\mu$l of the mixture through 300 $\mu$l of 20% sucrose at $12,000 \times g$ for 4 minutes. The platelet pellet is then separated from the rest of the mixture to determine platelet-bound radioactivity. Nonspecific binding is measured in mixtures containing an excess of unlabeled ligand. When binding curves are analyzed by Scatchard analysis, nonspecific binding is derived as a fitted parameter from the binding isotherm by means of a computerized program. To determine the concentration of each inhibitory compound necessary to inhibit 50% of fibrinogen binding to thrombin-stimulated platelets (IC$_{50}$), each compound is tested at 0.176 $\mu$gmol/liter (60 $\mu$g/ml). The IC$_{50}$ is derived by plotting residual fibrinogen binding against the logarithm of the sample compound's concentration.

II. Inhibition of Fibrinogen - Mediated Platelet Aggregation, which is essentially based on the method described in Blood, Vol. 66, No. 4, October 1985, pp. 846–952, and is as follows.

Human Platelets were isolated from freshly drawn whole blood and were suspended in 0.14 mol/L NaCl, 2.7 mmol/L K11, 12 mmol/L NaHCO$_3$, 0.42 mmol/L Na$_2$HPO$_4$, 0.55 mmol/L glucose, and 5 mmol/L Hepes, pH 7.35 at $2 \times 10^8$ platelets/ml. The suspension was incubated at 37° C. An aliquot of 0.4 ml of platelet suspension was activated by human thrombin at a final concentration of 2 $\mu$g/ml of thrombin for one minute. After one minute the reaction was stopped by a thrombin inhibitor. Serial dilution of the compound being tested was then added to the activated platelet, the reaction was allowed to proceed for one minute, followed by the addition of human fibrinogen at a final concentration of 60 μ/ml of fibrinogen. Platelet aggregation was then recorded by an aggregometer. Rate of aggregation was used to calculate IC$_{50}$.

Representative results of platelet aggregation inhibition are shown in Table I.

TABLE I

| | Inhibition of $^{125}$I-Fibrinogen Binding to Platelet IC$_{50}$ (μM) | Inhibition of Fibrinogen Mediated Platelet Aggregation | |
|---|---|---|---|
| | | IC$_{50}$ (μM) | % inhibition at 100 μM |
| N-(5-guanidinopentanoyl)-azetidin-(2S)-carboxyl-Asp—Val | 1.3 | 1.2 | 95** |
| N-(5-aminopentanoyl)-azetidin-(2S)-carboxyl-Asp—Val | >200 | 59 | 74 |
| N-(L-arginyl)-azetidin-(2S)-carboxyl-Asp—Val | 13 | 13 | 91 |
| N-[1-(L-arginyl)piperidin-2-yl-carbonyl]-L-aspartyl-L-valine | * | 28.6 | 73 |
| L-arginyl-L-prolyl-L-aspartyl-L-valine | * | >100 | 25 |

*Inhibited less than 50% at 50 μg/ml
**This compound showed 95% inhibition at 25 μm.

The compounds of the present invention may be orally or parenterally administered to mammals. The compound may be incorporated into pharmaceutical formulations having excipients suitable for these administrations and which do not adversely react with the compounds, for example, water, vegetable oils, certain alcohols and carbohydrates, gelatin and magnesium stearate. The pharmaceutical formulations containing an active compound of the present invention may be made into: tablets, capsules, elixirs, drops or suppositories for enteral administration; and solutions, suspensions or emulsions for parenteral administration.

In general, compound of this invention is administered in dosages of approximately 1 to 200 mg per dosage unit or higher. The daily dosage is approximately 0.02-5 mg/kg of body weight. It is to be understood, however, that the particular dose for each patient as usually depends on very diverse factors, such as the age, body weight, general condition of health, sex diet and the like of the patient, on the time and route of administration, on the rate of excretion, on the combination of medicaments and on the severity of the disease.

Having described the invention, it will be apparent to one of ordinary skill in the art that changes and modifications can be made thereto without departing from the spirit and scope of the invention as set forth herein.

What is claimed is:

1. A compound of the formula $$\begin{array}{c} O \\ \| \\ C-N \\ | \\ Y-CH \\ | \\ (CH_2)_m \\ | \\ NH-X \end{array} \begin{array}{c} (CH_2)_n \\ -C-NH-CH-C-Z \\ \| \quad | \\ O \quad CH_2COOH \end{array}$$

and pharmaceutically acceptable salts thereof, wherein:
X is H, amidino or $$\begin{array}{c} C-R; \\ \| \\ O \end{array}$$

Y is H, amino or $$\begin{array}{c} NH-C-R; \\ \| \\ O \end{array}$$

Z is naturally occurring L-amino acid bounded to the carbon atom at the a-amino position selected from the group consisting of: Val, Ser, Phe, Leu, Ile, Tyr, Trp, Arg, and Lys,
R is alkyl, aryl or aralkyl;
m is 0 and;
n is 1 through 2.

2. A pharmaceutical composition for the prophylaxis or treatment of abnormal thrombus formation in a mammal comprising a pharmaceutically acceptable carrier and a pharmaceutically effective amount of a compound of claim 1.

3. A method of preventing or treating thrombus formation in a mammal comprising the administration of the composition of claim 2.

4. N-(5-guanidinopentanoyl)-azetidin-(2S)-carboxyl-Asp-Val.

5. N-(5-aminopentanoyl)-azetidin-(2S)-carboxyl]-Asp-Val.

6. N-(L-arginyl-azetidin-(2S)-carboxyl-Asp-Val.

7. N-[1-(L-arginyl)piperidin-2-yl-carbonyl]-L-aspartyl-L-valine.

8. L-arginyl-L-prolyl-L-aspartyl-L-valine.

* * * * *